US006203824B1

(12) United States Patent
Banks et al.

(10) Patent No.: US 6,203,824 B1
(45) Date of Patent: Mar. 20, 2001

(54) CARBONYL SULPHIDE INSECTICIDE

(75) Inventors: Henry Jonathan Banks, Pialligo; Francis James Michael Desmarchelier, Queanbeyan; Ren Yonglin, Lyneham, all of (AU)

(73) Assignee: Commonwealth Scientific and Industrial Research Organisation, Campbell (AU)

( * ) Notice: Subject to any disclaimer, the term of this patent is extended or adjusted under 35 U.S.C. 154(b) by 0 days.

(21) Appl. No.: 08/967,073

(22) Filed: Nov. 10, 1997

Related U.S. Application Data

(63) Continuation of application No. 08/256,287, filed as application No. PCT/AU93/00018 on Jan. 15, 1993.

(30) Foreign Application Priority Data

Jan. 15, 1992 (AU) .............................. PL0426/92

(51) Int. Cl.[7] .......................... A01N 59/02; A01N 59/04; A61L 2/20; A23B 9/22
(52) U.S. Cl. ............................ 424/706; 424/40; 424/699; 424/DIG. 11; 426/319; 426/312; 422/32; 43/124; 43/125; 47/DIG. 10
(58) Field of Search .............................. 424/40, 706, 699, 424/DIG. 11; 426/319–320, 312; 514/706; 422/32; 43/124, 125; 47/DIG. 10

(56) References Cited

U.S. PATENT DOCUMENTS 4,250,156 * 2/1981 Takahashi et al. .................... 423/416

FOREIGN PATENT DOCUMENTS

| | | |
|---|---|---|
| 26744/88 | 6/1989 | (AU) . |
| 60062/90 | 2/1991 | (AU) . |
| 19506631 | * 8/1996 | (DE) . |
| 19606023 | * 8/1997 | (DE) . |
| 412471 | * 2/1991 | (EP) . |

OTHER PUBLICATIONS

S.M. Kluczewski, et al, "Deposition of Carbonyl Sulphide to Soils" —pp. 1295–1299, Atmospheric Enviroment—vol. 19, No. 8 (1985).
Kluczewski, et al., "Desposition of [355 ]—Carbonyl Sulfide to Vegetable Crops," Caplus Abstract, Accession No. 1985:518868 (1985).
Brown, et al., "Metabolism of [35S]—Carbonyl Sulfide in Perennial Ryegrass . . . " *Chemical Abstracts*, vol. 106, No. 1, Abstract No. 2949 (1987).
Ferm, R.J. "The Chemistry of Carbonyl Sulfide," *Chemical Reviews*, vol. 57, pp. 621–640. (1957).
G.E. Taylor, et al., "Phytotoxicity in Bush Bean of Five . . . ," *Chemical Abstracts*, vol. 101, No. 3, Abstract No. 18617 (1984).

(List continued on next page.)

Primary Examiner—John Pak
(74) Attorney, Agent, or Firm—Ladas & Parry

(57) ABSTRACT

The gaseous chemical compound, carbonyl sulphide, has hitherto been unknown as a fumigant for the control of insects and mites. Experiments have shown conclusively that carbonyl sulphide can be used as such a fumigant, with fumigation properties comparable to those of phosphine and methyl bromide. The effectiveness of carbonyl sulphide against insects (both adult and immature stages), mites, termites and moulds is demonstrated. In addition, its low absorbtion by grain, lower flammability than phosphine, lack of influence on seed germination, and apparent environmental safety make carbonyl sulphide particularly beneficial as a fumigant of stored grain. It may also be used to fumigate other stored produce (including perishable foodstuff), soil, timber and spaces (such as buildings) and any material likely to be infested by insects or mites, or act as a source of such infestation.

55 Claims, 1 Drawing Sheet

OTHER PUBLICATIONS

Figure 1:
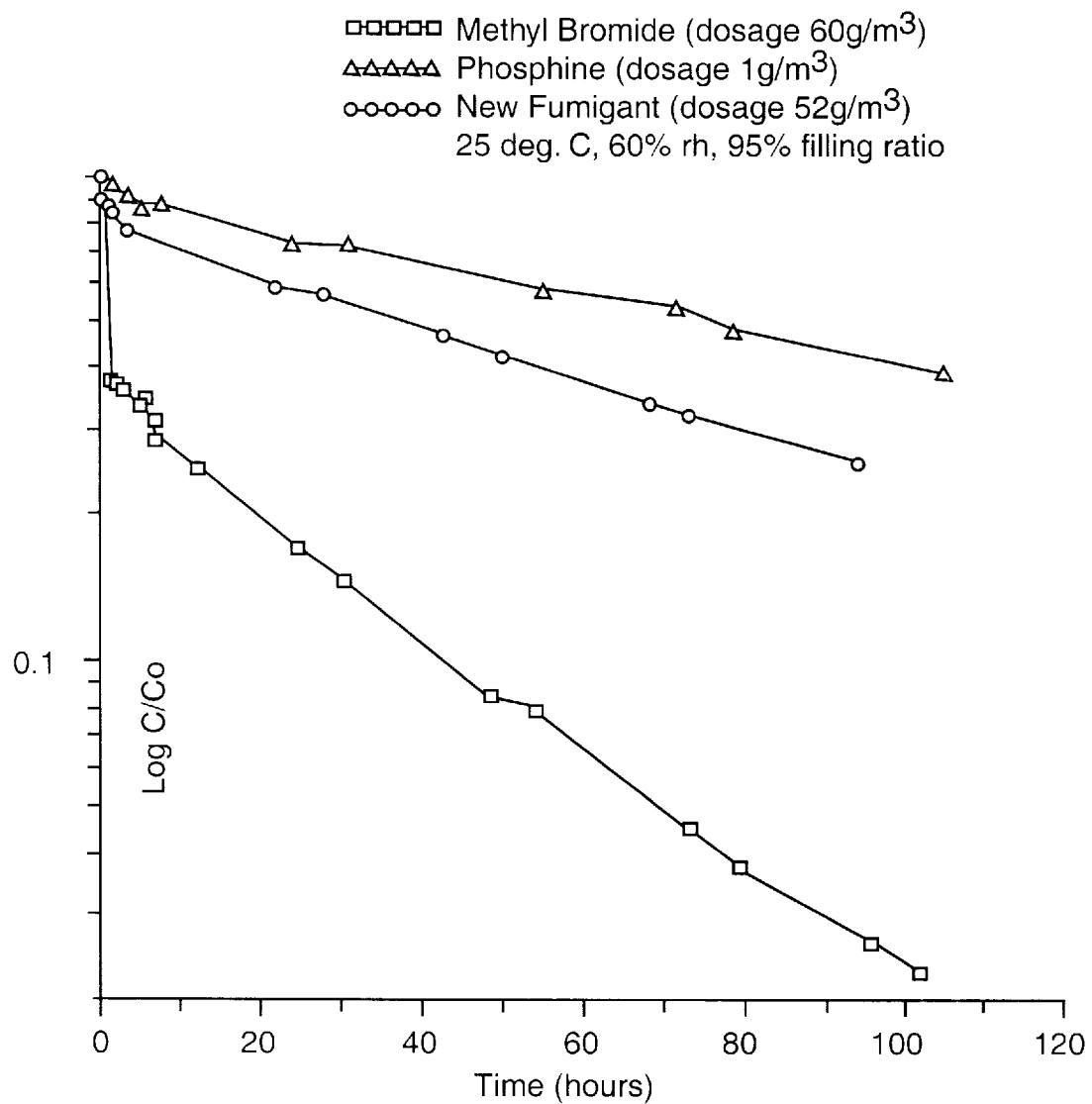

G.E. Taylor, et al., "Phytotoxicity in Bush Bean of Five . . .," *J. Environ. Qual.,* vol. 13, No. 2, pp. 224–230 (1984).

R. Fuerst, et al., "Gases Affecting Bacterial Survival," *Chemical Abstracts*, vol. 67, No. 15, pp. 305–312, Abstract No. 7129w (1966).

Brown et al., "Metabolism of [35S]—Carbonyl Sulfide in Perennial Ryegrass . . . " Biosis Abstract, Accession No. 87:109721, 1987.*

Perkow, W. Die Insektizide; Chemie, Wirkungsweise und Texizitat; 2. verb. und uberarb. Aufl. Heidelberg, Huthig, 1968. 24 cm, 565 blz., afbn., lit.cpgn., tabn., pp. 467–487.

Abeles, F.B. et al. "Inhibition of *Monilina Fructicola* and *Penicillium expansum* by carbonyl sulfide," Phytopathology, vol. 72, No. 6, p. 705, Jun. 1982.*

Sittig, M. Handbook of Toxic and Hazardous Chemicals and carcinogens. NOYES Publications (NJ), pp. 192–193, 1985.*

West, T.F. et al. Chemical Control of Insects. Chapman and Hall Ltd. (London), pp. 37–39, 1951.*

Kluczewski et al., "Deposition of [35S]—Carbonyl Sulfide to vegetable crops," Radiation Protection Dosimetry, vol. 11, No. 3, 1985, pp. 173–177.*

Brown et al., "Metabolism of [35S]—Carbonyl Sulfide in perrenial Rygrass . . . " Environmental and Experimental Botany, vol. 26, No. 4, 1986, pp. 355–264.*

Biobusiness Abstract, Accession No. 85:24936 (1985).*

* cited by examiner

CARBONYL SULPHIDE INSECTICIDE

This is a continuation of application Ser. No. 08/256,287 filed Sep. 28, 1994, now abandoned, which is a U.S. National Stage of PCT/AU93/00018, filed Jan. 15 1993.

TECHNICAL FIELD

This invention concerns gaseous fumigants. More particularly, it concerns the gas carbonyl sulphide (COS), which has also been termed carbon oxysulphide, as a fumigant.

BACKGROUND OF THE INVENTION

Fumigants are widely used for the disinfestation, and protection against infestation, that is usually required to protect particulate materials (such as grain) and other stored produce (including durable and perishable foodstuff), porous bulk materials (for example, soil or timber) and spaces (typically, empty buildings). An ideal fumigant should be toxic to insects, mites, nematodes, bacteria, fungi and moulds. It should be effective in low concentrations. It should have a low absorbtion by materials in the fumigated region. It should have a low mammalian toxicity and leave either no residue or an inert residue. In addition, the ideal fumigant should present no difficulties as far as safe handling is concerned, and it should not adversely affect the commodity or space that is being fumigated.

No fumigant meets all of these "ideal" criteria. The two fumigants most commonly used in the fumigation of grain, other particulate materials, fruit and timber are phosphine and methyl bromide. Phosphine is the preferred fumigant for grain stores and the like because it is effective against grain pests and leaves little residue (which is essentially a harmless phosphate). However, phosphine is spontaneously combustible when its concentration exceeds a relatively low value.

Methyl bromide is more toxic to grain pests than phosphine when used for short periods of fumigation, but phosphine is more toxic to grain pests when long term fumigation is effected. Methyl bromide has a lower flammability than phosphine, but recent work has shown that methyl bromide depletes the ozone layer. Thus approval of methyl bromide as a fumigant is currently under review, following the Montreal protocol.

Other fumigants that have been used against grain pests include acrylonitrile, carbon disulphide, carbon tetrachloride, chloropicrin, ethylene dibromide, ethylene dichloride, ethylene oxide, hydrogen cyanide and sulphuryl fluoride. It will be noted that a halogen is present in the majority of these "conventional" fumigants, none of which has the "ideal" fumigant properties.

For many years, there has been a. constant seeking of new fumigants and there is no doubt that the quest for improved fumigants will continue.

DISCLOSURE OF THE PRESENT INVENTION

The prime object of the present invention is the provision of a new fumigant that has properties which make it a viable alternative to the conventional fumigants, particularly in the control of insects, mites and moulds.

This objective is achieved by the use of carbonyl sulphide as a fumigant.

Carbonyl sulphide is a well-known compound. It is a gas at STP (Standard Temperature and Pressure), with a boiling point of −50.2° C. It is colourless, flammable (but not as flammable as phosphine), and soluble in water. Its solubility in water is 1.4 grams per litre at 25° C., compared with the aqueous solubilities of 13.4 grams per litre and 2.2 grams per litre for, respectively, methyl bromide and carbon disulphide (phosphine has been reported to be "sparingly soluble" in water). When in aqueous solution, it slowly decomposes. Commercially, carbonyl sulphide is normally supplied in liquefied form in cylinders at about 160 p.s.i.g. However, it occurs naturally, being the major sulphur species in the atmosphere (where it occurs uniformly in the troposphere and lower troposphere at a concentration of 1.3 micrograms per cubic metre) and part of the natural sulphur flux in soils and marshes. Carbonyl sulphide is also formed from the anaerobic degradation of manure and compost and is present in most pyrolysis products and in oil refineries.

As a consequence of its role in the sulphur cycle, its presence in pyrolysis products and its use as a chemical feedstock, carbonyl sulphide has been widely studied, and its properties and uses are well known. However, an extensive review of the technical literature, and a Dialog computer-based evaluation search (conducted in the files of *CAB Abstracts* 1972–1991, *Biosis Previews* 1969–1991, *Life Sciences Collection* 1978 to 1991, *Agricola* 1970 to 1991, *Agris International* 1974 to 1991, *EuroDean Directors of Agrochemical Products* and *Oceanic Abstracts* 1964 to 1991), has revealed no use or contemplated use of carbonyl sulphide as a fumigant, and no reference to the insect toxicity of carbonyl sulphide. A separate manual search of *Chemical Abstracts* extended back to the year 1900, but found no reference to carbonyl sulphide as a fumigant.

It is known that carbonyl sulphide is a mammalian toxic gas. In the article by Robert J Ferm entitled "The Chemistry of Carbonyl Sulfide", which was published in *Chemical Review*, volume 57, 1957, pages 621 to 637, three references are given in support of the statement at page 627 that:

"Cold blooded animals show more resistance to carbonyl sulfide than do warm-blooded animals. Mice and rabbits die quickly when they are exposed to air containing more than 0.3 per cent carbonyl sulfide."

And in the current *Matheson Gas Products Catalogue*, in the section entitled "Carbonyl sulfide" (pages 115 to 117), it is stated that (page 115):

"Carbonyl sulphide acts principally upon the central nervous system, with death resulting mainly from respiratory paralysis. Rabbits showed some ill effects after exposure of one half hour to 1300 ppm. With mice, death occurred in ¾ minute when they were exposed to 8900 ppm, in 1½ minutes on exposure to 2900 ppm, and in 35 minutes on exposure to 1200 ppm. Sixteen minutes exposure to 900 ppm caused no perceptible effects."

However, it is known that gaseous compounds which are lethal to humans and smaller mammals, and also to cold-blooded vertebrates, may not be toxic to insects, moulds, mites and the like. One example of such a mammalian toxic gas is carbon monoxide. Thus, simply because carbonyl sulphide has a measured toxicity to mammals, it would be incorrect to conclude that carbonyl sulphide will also kill insects, moulds, mites and the like.

The present inventors, therefore, were surprised to find that carbonyl sulphide is useful as a fumigant. However, the present inventors have now established that when carbonyl sulphide is used as a fumigant, it may be applied undiluted, in a manner which allows it to mix with the atmosphere within the system under treatment, or it may be applied in a mixture with an inert diluent gas. The diluent gas will be used when a more dilute form of the fumigant is to be dispensed, or as an inhibitor to reduce flammability of the carbonyl sulphide. The diluent gas will normally be air, although other suitable carrier gases may be used.

The present invention also encompasses a method of fumigation of particulate materials, commodities, timber, spaces and soils which comprises applying gaseous carbonyl sulphide thereto.

Further details will now be provided, by way of example only, in the following discussion of the properties of carbonyl sulphide as a fumigant, including examples which demonstrate such properties.

DISCUSSION OF THE INVENTION

The effectiveness of a fumigant is usually expressed as a "CT product", which is the concentration×time product for a specified effectiveness (usually for $LC_{95}$ or $LC_{99}$, which are the lethal concentrations—doses—for 95 per cent and 99 per cent, respectively, of the population against which the fumigant is directed), expressed in milligram hours per litre. Normally, the temperature at which the fumigant is used is also given, for, in general, the higher the temperature of treatment with a fumigant, the lower the dose or concentration that is necessary to achieve a required effectiveness.

The concentration×time products, expressed in the usually adopted terms of $LD_{90}$, $LD_{95}$ or $LD_{99}$ (although strictly speaking these figures are $L(C\times T)_{90}$, $L(C\times T)_{95}$ and $L(C\times T)_{99}$ values), for eleven previously known fumigants that are still in use against grain pests, are shown in Table 1. The data in Table 1, relating to eight species of grain pests, has all been obtained from prior art publications.

The present inventors have conducted numerous experiments to demonstrate the efficacy of carbonyl sulphide as a fumigant. A number of these experiments are detailed in the following Examples. In each case when carbonyl sulphide was used, the gas was produced by the reaction of potassium thiocyanate with sulphuric acid, as described by A Stock and E Kuss in their paper in *Chemische Berichte der deutchen Gesellschaft*, Volume 50, 1917, page 159. This method of production is recommended by R J Ferm in his aforementioned paper in *Chemical Review*, volume 57, 1957. The carbonyl sulphide thus produced was washed with a solution of lead acetate in water, to remove hydrogen sulphide. The purity of the carbonyl sulphide was measured using a GOW-MAC (Model 40-001) gas density detector; it typically had a purity between 80 per cent and 90 per cent V/V, with the major impurity being carbon dioxide. No hydrogen sulphide or sulphur dioxide was detected.

The fumigant concentrations in the experiments were analysed using a Shimadzu GC6 gas chromatograph, with a flame ionisation detector. Column conditions were 20 per cent 0V 101 on Gas Chrom Q at 42° C. column temperature, and injection temperature of 105° C.

The following species were subjected to tests of the efficacy of carbonyl sulphide as a fumigant: *Tribolium castaneum* (Herbst), (Coleoptera, tenebrionidae), strain CTC4; *T.confusum* (Jacq du Val) (Coleoptera, Curculionidae), strain CLS2; *Rhyzopertha dominica* (F) (Coleoptera, Bostrichidae), strain CRD2; *Oryzaephilus surinamensis* (L) (Coleoptera, Silvanidae), strain NOS4; *Ephestia cautella* (Walker) (Noctuidae, Pyralidae), strain CEC2; *Bactrocera tyroni* (Froggat), formerly *Dacus tyroni* (Diptera, Tephrididae), collected Wollongong 1989; *Liposcelis bastrychophilus; Lepidoalyphus destructor* (Schrank); *Coptotermes acinaciformis* (Froggat) (Isoptera, Rhinotermitidae); and *Cryptotermes domesticus* (Haviland, Isoptera, Kalotermitidae)

EXAMPLE 1

Tests of the Efficacy of Carbonyl Sulphide to Control External Stages of Stored-product Insects.

To test the effectiveness of carbonyl sulphide against the external stages of these stored product insects, glass serum vials (bottles) having a capacity of approximately 120 mL were used. These vials had a crimp top and were closed with a cap which permitted gas injection using a syringe (a "Mininert" valve). The bottles were left open in an atmosphere of 55 per cent relative humidity at the temperature at which the bioassay was to be performed (usually 25° C. or 30° C.).

To test the effectiveness of carbonyl sulphide against live insects, between 25 and 35 insects were added to each vial, which was then closed by its cap. A quantity of air, equal to the volume of gas to be injected, was then withdrawn from each bottle and the same volume of gas was injected into it. The bottle was kept at a constant temperature for the duration of the bioassay, which was usually 6 hours or 24 hours. At the end of this period, the insects in each bottle or vial were transferred to respective 60 mL glass jars, which contained 20 grams of wheat. The insects remained in the glass jars with the wheat for 14 days before the mortality assessment was made. All assays were replicated three or four times, and were accompanied by a control assay, in which no carbonyl sulphide was injected into the bottles containing the insects.

In the mortality assessment, the adult insects were classified as dead if they failed to respond to any stimuli. The control assay mortality was always assessed.

The assays of the effectiveness of carbonyl sulphide against the pupae of insects were conducted in a manner similar to the adult insect assays, except that, after treatment in the bottle, the pupae were transferred to glass jars containing 10 grams of flour. The mortality of the pupae was assessed as an inability of the pupae to become adults. The bioassays with pupae were all replicated three or four times, with control assays.

Corresponding assays of the effectiveness of carbonyl sulphide against insect larvae were conducted in the same manner as the bioassays with pupae, except that the mortality of the larvae was assessed, like that of adult insects, as an inability to respond to any stimuli. Larvae which successfully pupated after treatment were assessed as survivors.

Tests of the effectiveness of carbonyl sulphide against the eggs of insects were performed with the eggs on strips of filter paper. These strips were each approximately 1 cm×5 cm, cut from S & S Rundfilter Nr 593, 90 mm diameter, filter papers, marketed by Schleicher and Schuell. The eggs of most species were oviposited directly onto the filter paper, after the adult insects had been added to a thin layer of wheat, brewers yeast and filter paper. In the case of *Tribolium casteneum* (Herbst), the eggs were oviposited on superfine flour and were recovered by sieving. The eggs were then transferred with a single hair brush, dipped into a 30 per cent sucrose solution, to strips of filter paper which were covered with double-sided adhesive paper—"Double Stick Tape", sold as "Scotch brand" (Trade Mark), marketed by 3M Consumer Products Group.

The adult insects were removed after 16 hours on the medium. Some eggs were dosed with carbonyl sulphide within 24 hours of the start of oviposition, these eggs being classified as "0–1 day old eggs". Other eggs were kept for a further four days, to generate "4–5 days old eggs", before being dosed with carbonyl sulphide.

Typically, 20 to 30 eggs were deposited on each strip of filter paper. The strips of filter paper, with the deposited eggs, were placed in respective glass vials (bottles) of the same type as those that were used to test the effect of carbonyl sulphide on adult insects, and were dosed with carbonyl sulphide in the same manner as the adult insects. After the exposure to carbonyl sulphide, the eggs were placed in a covered Petrie dish and stored at 30° C. for seven days. At the end of this storage period, the numbers of hatched and unhatched eggs were counted, using a Nikon stereo microscope, equipped with a cold light source. The eggs that had failed to hatch were classified as dead. All assays using eggs were performed in triplicate, with a corresponding control (untreated by carbonyl sulphide) bioassay.

The results obtained with the bioassays for external stages are summarised in Table 2, which records the species, the stage of the insect (adult, pupae, larvae or eggs), the period of exposure to carbonyl sulphide, the temperature at which the bioassay was performed, the $Lc_{95}$ values (expressed in milligrams hours per litre—$mg.h.L^{-1}$), and the minimum effective tested dose. The minimum effective tested dose is the minimum tested dose that killed all insects in assays involving at least 100 insects. Entomologists will find that a comparison of the results in Table 2 with the prior art data collated in Table 1 demonstrates that the effectiveness of carbonyl sulphide against the external stages of insects is comparable to that of other, known fumigants.

The data presented in Table 2 clearly demonstrates the effectiveness of carbonyl sulphide against all external stages of the insects listed in Table 2.

EXAMPLE 2

The Effectiveness of Carbonyl Sulphide Against Internal Stages of Stored-product Insects.

In a series of experiments, adults of the grain pest *Rhyzopertha dominica* were allowed to oviposit for 4 to 5 weeks on 1,000 grams of wheat, maintained at 30° C. and having a moisture content of 12 per cent. In each experiment, the adults were removed from the wheat, which was then divided into three portions; two for dosing with carbonyl sulphide and one for use as a control. Each portion of wheat was then placed in a glass jar having a capacity of 1.1 litre, and the jar was sealed with a screw cap which had been fitted with a septum. A dose of carbonyl sulphide in the range of from 8 mg per litre to 45 mg per litre was injected through the septum. After the assay period (for example, 24 hours), the screw cap was replaced with filter paper, to enable the fumigant to be aired. The wheat was then stored at either 25° C. or 30° C. The emerging adults were counted at weekly intervals over a period of from four to five weeks. Replication of each experiment was performed by repeating the entire procedure.

The results of this series of experiments are given in Table 3. It will be noted that an exposure for 24 hours to a dose of 8 mg per litre of carbonyl sulphide gave, on average, 93.4 per cent control of all immature stages of *R. dominica*. The most tolerant stage was probably pre-pupae (that is, those insects which emerged in 7 to 14 days after dosing).

A second series of experiments, performed in the same manner but with exposure of the wheat to carbonyl sulphide for periods of 6 hours, 24 hours and 48 hours, produced the results recorded in Table 4. It will be noted, from these results, that extending the exposure time to a single dose of carbonyl sulphide increased the mortality of the internal stages, indicating that the toxic effect of carbonyl sulphide on insects in whole grain was not rapidly destroyed by sorption of the carbonyl sulphide.

A third series of experiments was performed to investigate the efficacy of carbonyl sulphide in the control of the internal stages of the grain pest *Sitophilus oryzae*. The same procedure was adopted, with carbonyl sulphide doses in the range of from 15 mg per litre to 91 mg per litre, and with exposures to a single dose ranging from 6 hours to 72 hours. The results of these experiments are given in Tables 5, 6 and 7.

A fourth series of experiments was performed, using the procedure of this Example, to investigate the relative efficacies of carbonyl sulphide, carbon disulphide and ethyl formate against the internal immature stages of *S. oryzae* and *R. dominica* in whole grain. The outcome of this series of experiments is shown in Table 8. The superiority of carbonyl sulphide as a controller of the internal stages of these grain pests is clearly evident.

EXAMPLE 3

The Effectiveness of Carbonyl Sulphide in the Control of Stored-product Mites and Psocids.

A series of assays was conducted to demonstate the effectiveness of carbonyl sulphide against adult wheat mites and psocids (species *Liposcelis bostrychophilus*). The methodology of the assays of adult external stages of stored-product insects, described above in Example 1, was used, except that 3 grams of wheat (containing 18 per cent moisture) and approximately 100 mg of brewers yeast were added to the glass jars before the addition of approximately 200 psocids. After exposure of the psocids to carbonyl sulphide for either six hours or 24 hours, the sealing caps were removed from the jars and, after 1 hour of airing, the jars were closed with thin plastic material. The assays were conducted at 25° C., 75 per cent relative humidity. The number of mobile mites was counted at the end of the exposure to the carbonyl sulphide and the mortality was assessed after a holding period of five days.

The results of these experiments with adult psocids and mites (*Lepidoglyhus destructor*) are shown in Tables 9 and 10, with some of the information obtained from this data being included in Table 2.

In a separate experiment, 200 psocids in a glass container were exposed to a dose of 5 mg per litre of carbonyl sulphide for one hour. At the end of that one hour exposure to carbonyl sulphide, all 200 of the psocids were dead.

EXAMPLE 4

The Efficacy of Carbonyl Sulphide in the Control of Fruit Flies.

Bioassays of the effect of carbonyl sulphide on the external immature stages of the Queensland fruit fly, *Bactrocera tyroni* (Diptera: Tephritidae) were conducted in the same manner as the assays of the immature external stages of stored-product insects in Example 1, except that (a) when using eggs, the filter paper strips were damp when subjecting the eggs to a dose of carbonyl sulphide, and (b) one drop of water was added to each jar for larvae prior to the addition of the insects.

The assays with eggs, feeding larvae and pupae of *B. tyroni* were conducted at 30° C. The results are shown in Tables 11, 12 and 13 for, respectively, pupae, late instar larvae and eggs of *B. tyroni*.

EXAMPLE 5

The Use of Carbonyl Sulphide to Control Termites

Adult termites and nymphs of the species *Coptotermes acinaciformis* (Froggat) (Isoptera, Rhinotermitidae), and *Cryptotermes domesticus* (Haviland, Isoptera, Kalotermitidae) were exposed to carbonyl sulphide in the same manner as the adult stored-product insects in Example 1, except that damp filter paper (Whatmans No 1, diameter 4.25 cm) was added to each jar before the addition of insects. The results obtained with this series of experiments with adults and nymphs of *Coptotermes acinaciformis* are recorded in Tables 14 and 15.

EXAMPLE 6

The Effect of Carbonyl Sulphide on Seed Germination

To investigate whether carbonyl sulphide affects the germination of seeds, grains of Australian standard white wheat and malting barley were conditioned to 12 per cent and 16 per cent moisture, as determined by the ISO air oven method. The grain samples were each dosed for 24 hours with carbonyl sulphide in concentrations of 0.5 per cent V/V, 1.0 per cent V/V and 5.0 per cent V/V. At these concentrations, the corresponding nominal concentration× time products were 300 mg hours per litre, 600 mg hours per litre and 3,000 mg hours per litre.

In all of these experiments, no effect on seed germination or vigour was detected. Table 16 records the results obtained with wheat at 16 per cent moisture content.

EXAMPLE 7

The Sorption of Carbonyl Sulphide on Grains

Sorption studies using grains of Australian standard white wheat and Calrose rice were carried out using glass serum vials of capacity 120 ml, each equipped with a cap having a "Mininert" valve to permit gas injection. The moisture contents of the grain samples were measured with an electronic meter (a Marconi meter). The samples of grain were then used to fill the vials to levels of, respectively, 25 per cent, 50 per cent and 95 per cent. The vials were then held at 25±1° C. A volume of air equal to the fumigant dose to be used was removed from each vial, then the same volume of carbonyl sulphide was added to the vial. The concentration of carbonyl sulphide was measured with time and analysed to evaluate the decay of carbonyl sulphide.

An example of the raw data obtained in the course of these experiments is provided in Table 17. It will be noted that for a filling ratio of 0 per cent (that is, no wheat in the vial), recoveries 0.25 hour after dosing were 98.4 per cent of the calculated applied dose. This is a very high level of recovery. The decline in fumigant concentration from vials containing no grains, after 93.9 hours of testing, in replicated experiments, was always, in the range of from 1.2 per cent to 1.5 per cent, which indicates a high degree of sealing of the vials. The results obtained from these experiments are consistent with a rapid initial uptake of some fumigant by the grain, followed by declining residues of fumigant, in a manner proportional to the amount of grain in the vial.

Similar experiments were conducted with methyl bromide and phosphine as the fumigant, to obtain comparative sorption data. The results are shown in FIG. 1. Clearly carbonyl sulphide is absorbed much less strongly than methyl bromide, and slightly more strongly than phosphine. This indicates that carbonyl sulphide may be used for long exposure fumigation.

EXAMPLE 8

The Effectiveness of Carbonyl Sulphide as a Mould Inhibitor

In a test of the effectiveness of carbonyl sulphide as a mould inhibitor, a number of samples of wheat, containing 31 per cent moisture (w/w, wet basis) were placed in sealed containers (glass jars). Some containers held only the wheat sample and air. Other containers held the wheat sample and air containing from 2.5 per cent to 10.0 per cent (by volume) of carbonyl sulphide. All of the sealed containers were kept at 35° C. for seven days. After two days of this storage, some of the wheat in the sealed containers which held no fumigant was noticeably discoloured. After seven days, all of the wheat in the containers without fumigant was discoloured by growth of mould on the grains. However, no discolouration occurred of the wheat which was in the containers which also held carbonyl sulphide in concentrations in the range from 4.5 per cent to 10.0 per cent (by volume).

EXAMPLE 9

Investigation of how the Period of Exposure Affects the Concentration of Carbonyl Sulphide.

Samples of a mixed culture of *Sitophilus oryzae* were exposed to different concentrations of carbonyl sulphide for periods ranging from 6 hours to 168 hours, using the same technique as that described in Example 2. The results of this series of experiments are shown in Table 18. It will be seen that carbonyl sulphide is an effective control of this insect over a large range of concentrations and for a wide range of exposure periods.

EXAMPLE 10

Investigation of the Use of Carbonyl Sulphide to Fumigate Soil

Three samples of soil—designated samples A, B and C—were taken from a vegetable garden. Sample A was taken from a compost heap in the garden. The moisture contents of the samples A, B and C were, respectively, 29.4 per cent, 25.8 per cent and 27.1 per cent.

Three glass vials (jars), each of capacity 120 mL, were approximately half-filled with soil from each of the samples A, B and C. Each vial was then fitted with a "Mininert" valve. Carbonyl sulphide was applied to two of the three vials containing soil from a sample. The third vial or jar was left untreated, as a control. In addition, 1 kilogram of soil from sample B was placed in a glass jar of capacity 1.8 L, fitted with a lid having a septum through which carbonyl sulphide was injected.

All of the jars (that is, the vials of 120 mL capacity and the 1.8 L jar) were stored at 27° C. for 20 hours. During this storage period, the concentration of carbonyl sulphide in each jar was measured. From the measurements of the concentration of carbonyl sulphide during the storage period, the following results were obtained:

(a) two minutes after the injection of carbonyl sulphide, the concentration of carbonyl sulphide had an average value of 62 per cent of the calculated initial concentration, indicating a rapid uptake of carbonyl sulphide by the moist soil;

(b) five hours after the injection of carbonyl sulphide, the jars contained (on average) 18 per cent of the calculated initial concentration; and (c) after 20 hours, the average concentration of carbonyl sulphide was 5.9 per cent of the calculated initial concentration.

At the end of the storage period, the lids or caps were removed and the jars were left open to the air. The efficacy of the carbonyl sulphide was assessed by comparing the number of nematodes in the controls with those in the fumigated soils. The results obtained are summarised in Table 19.

It is clear from Table 19 that carbonyl sulphide effectively removes nematodes from soil.

EXAMPLE 11

Assessment of Carbonyl Sulphide as a Fumigant Relative to Phosphine and Methyl Bromide It was noted in the introduction to this specification that there is no "ideal" fumigant. The selection of a fumigant is made by assessing its advantages and disadvantages. The present inventors have ranked the commonly used fumigants methyl bromide and phosphine with carbonyl sulphide in respect of mammalian toxicity, insect toxicity (short and long exposures), environmental safety and flammability.

For each parameter, 1 was taken as the best ranking and 3 the worst ranking. The results of this assessment are as follows:

|  | Relative ranking | | |
|---|---|---|---|
| Parameter | Methyl bromide | Phosphine | Carbonyl sulphide |
| Mammalian toxicity | 3 | 2 | 1 |
| Insect toxicity | | | |
| short exposures | 1 | 3 | 2 |
| long exposures | 2 | 1 | 3 |
| Environmental safety | 3 | 2 | 1 |
| Flammability | 1 | 3 | 2 |

The mammalian toxicity ranking was based on TLV values, and the flammability was assessed by reference to flammability limits in air. Methyl bromide was ranked last in the category "environmental safety" because of its effect on the ozone layer, and carbonyl sulphide was ranked above phosphine in this category because there is an absence of knowledge about the environmental fate of phosphine and reaction mechanisms of phosphine in the environment.

It is clear that carbonyl sulphide is a viable alternative to methyl bromide and phosphine as a fumigant. It can be used for short term fumigation (which is not possible with phosphine) and for long periods—up to 35 days or more (which is not possible with methyl bromide). In addition, it will be apparent to entomologists that registration of carbonyl sulphide as a "new" fumigant should be a relatively inexpensive exercise in view of the extensive knowledge already obtained regarding carbonyl sulphide.

TABLE 1

Concentration x time products of certain fumigants required for the control of various species of insects

| Insect | Oryzsephilus surinamensis | Rhyzopertha dominica | Sitophilus granarius | Sitophilus oryzae |
|---|---|---|---|---|
| Insect | Adults | Adults | Adults | Adults |
| Fumigant | $LC_{95}$ 6 h. 21° C. | $LC_{95}$ 6 h. 21° C. | $LC_{99}$ 5 h. 25° C. | $LC_{95}$ 6 h. 21° C. |
| Acrylonitrite | 8.4 | 8.4 | 11.0 | 10.8 |
| Carbon disulphide | 408.0 | 294.0 | 325.0 | 300.0 |
| Carbon tetrachloride | — | — | 495.0 | 220.0 |
| Chloropicrin | 19.2 | 15.6 | 150.0 | 23.4 |
| Ethylene dibromide | 19.2 | 37.2 | 34.5 | 60.0 |
| Ethylene dichloride | 462.0 | 636.0 | 230.0 | 738.0 |
| Ethylene oxide | 60.0 | 69.6 | 36.0 | 62.0 |
| Hydrogen cyanide (HCN) | 7.2 | 15.6 | 67.5 | 60.0 ($LD_{99}$) 5 h 25° C. |
| Methyl bromide | 40.8 | 33.0 | 28.0 | 30.0 ($LD_{99}$) |
| Phosphine (24 hr exposure 27° C.) | 0.96 ($LD_{99}$) | 0.6 ($LD_{99}$) | 1.01 | 0.36 ($LD_{99}$) |
| Sulphuryl fluoride | — | — | 17.5 | — |

| Insect | Tenebroides mauritanicus | Tribolium confusum | Tribolium castaneum | Trogoderma granarium |
|---|---|---|---|---|
| Insect Fumigant | Larvae $LC_{99}$ 5 h. 21° C. | Adults $LC_{99}$ 5 h. 25° C. | Adults $LC_{90}$ 6 h. 24° C. | Larvae $LC_{95}$ 8 h. 21° C. |
| Acrylonitrile | 40.0 | 19.5 | — | 48.0 |
| Carbon disulphide | 828.00 | 560.00 | — | 696.0 |
| Carbon tetrachloride | 400.00* | 025.0 | 600.0 | — |
| Chloropicrin | 56.00 | 57.5 | 14.0 | 96.0 |
| Ethylene dibromide | 125.00 | 31.0 | 22.0 ($LD_{95}$) 4 h. 27° C. | 80.0 |
| Ethylene dichloride | 1728.0 | 365.0 | 462.0 | 2080.5 |
| Ethylene oxide | 175.0 | 127.5 | 135.0** | 176.0 5 h. 25° C. |
| Hydrogen cyanide (HCN) | 66.5 | 5.55 | 2.4 ($LD_{95}$) | 26.4 |
| Methyl bromide | 115.0 | 64.0 | 62.0 ($LD_{95}$) | 136.0 h. 27° C. |
| Phosphine (24 hr exposure 27° C.) | 5.0 approx. | 0.48 | 11.5 | 331.0 100% mort. 72 h 21° C. |
| Sulphuryl fluoride | 81.5 | 55.0 | — | — |

*$LD_{50}$
**$LD_{99}$

TABLE 2

Toxicity of carbonyl sulphide to insects and mites

| Species | Stage | Exposure (h) | Temperature (° C.) | $LC_{95}$ (mg h $L^{-1}$) | Minimum effective tested dose (mg h $L^{-1}$) |
|---|---|---|---|---|---|
| R. dominica | adult | 6 | 25 | 38 | 68.7 |
| T. castaneum | | 6 | 25 | 82 | 108 |
| | | 24 | | 297 | |

TABLE 2-continued

Toxicity of carbonyl sulphide to insects and mites

| Species | Stage | Exposure (h) | Temperature (° C.) | $LC_{95}$ (mg h $L^{-1}$) | Minimum effective tested dose (mg h $L^{-1}$) |
|---|---|---|---|---|---|
| S. oryzae | | 6 | 25 | 99 | 112 |
| | | 24 | | 264 | |
| O. surinamensis | | 6 | 25 | 198 | 240 |
| | | 24 | 30 | | 240 |
| T. confusum | | 6 | 25 | 111 | 146 |
| L. destructor | | 6 | 27 | | 120 |
| | | 24 | | 240 | |
| psocids (L. bostrychophilus) | | 6 | 25 | | 22.5 |
| T. castaneum | pupae | 6 | 30 | 290 | 360 |
| | | 24 | 30 | 490 | 600 |
| E. cautella | | 24 | 27 | | 480 |
| B. tyroni | | 6 | 27 | | 360 |
| | | 24 | 27 | 440 | 600 |
| T. castaneum | larvae | 6 | 25 | 270 | 300 |
| | | 24 | 30 | | 480 |
| E. cautella | | 6 | 30 | | 240 |
| | | 24 | | 410 | 480 |
| O. surinamensis | | 6 | | 210 | 300 |
| B. tyroni | | 6 | 27 | | 180 |
| | | 24 | 27 | | 360 |
| R. dominica | eggs | | | | |
| | 0–1 d | 24 | 30 | 145 | 192 |
| | | 6 | | 102 | 144 |
| | 2–3 d | 24 | | | 144 |
| | 4–5 s | 24 | | | 120 |
| T. castaneum | 0–1 d | 24 | | 520 | 600 |
| | | 6 | | 430 | 480 |
| | | 48 | | | 360 |
| O. surinamensis | 0–1 d | 24 | | 495 | 600 |
| | | 6 | | | 420 |
| B. tyroni | 2–8 h | 24 | | 460 | 600 |
| E. cautella | 0–1 d | 24 | | | 600 |
| | | 6 | | | 720 |
| S. oryzae | 0–1 d | 24 | | | 600 |

TABLE 3

Control of immature stages of R. dominica at 25° C. or 30° C. after 24 h exposure

| Time after dosing before emergence (days) | Dose Low (mg $L^{-1}$) | Dose High | Temp (° C.) | No. emerging in Control | No. emerging in Low dose | No. emerging in High dose | % reduction Low dose | % reduction High dose |
|---|---|---|---|---|---|---|---|---|
| 0–7 | 8 | 16 | 25 | 0 | 0 | 0 | — | — |
| 7–14 | 8 | 16 | | 95 | 0 | 0 | 100 | 100 |
| 14–21 | | | | 294 | 12 | 0 | 95.9 | 100 |
| 21–28 | | | | 343 | 3 | 0 | 99.1 | 100 |
| 28–35 | | | | 360 | 4 | 0 | 98.8 | 100 |
| 0–35 | | | | 1092 | 19 | 0 | 98.3 | 100 |
| 0–7 | 15 | 45 | 25 | 77 | 4 | 0 | 94.8 | 100 |
| 7–14 | | | | 121 | 15 | 0 | 87.6 | 100 |
| 14–21 | | | | 123 | 4 | 0 | 96.7 | 100 |
| 21–28 | | | | 928 | 2 | 0 | 99.8 | 100 |
| 0–28 | | | | 1249 | 25 | 0 | 98.3 | 100 |
| 0–7 | 8 | 24 | 25 | 0 | 0 | 0 | — | — |
| 7–14 | | | | 69 | 0 | 0 | 100 | 100 |
| 14–21 | | | | 284 | 8 | 0 | 97.2 | 100 |
| 21–28 | | | | 253 | 11 | 0 | 95.6 | 100 |
| 28–35 | | | | 184 | 6 | 0 | 95.7 | 100 |
| 7–35 | | | | 790 | 25 | 0 | 96.8 | 100 |
| 0–7 | 8 | 25 | 30 | 14 | 1 | 0 | 92.8 | 100 |
| 7–14 | | | | 284 | 24 | 0 | 90.9 | 100 |
| 14–21 | | | | 234 | 6 | 0 | 97.4 | 100 |
| 21–28 | | | | 265 | 2 | 0 | 99.2 | 100 |
| 0–28 | | | | 797 | 33 | 0 | 95.9 | 100 |
| 0–7 | 8 | 25 | 25 | 131 | 29 | 0 | 77.9 | 100 |
| 7–14 | | | | 265 | 84 | 1 | 68.3 | 99.6 |
| 14–21 | | | | 244 | 38 | 0 | 84.4 | 100 |

TABLE 3-continued

Control of immature stages of *R. dominica* at 25° C. or 30° C. after 24 h exposure

| Time after dosing before emergence (days) | Dose Low (mg L⁻¹) | High | Temp (° C.) | No. emerging in Control | Low dose | High dose | % reduction Low dose | High dose |
|---|---|---|---|---|---|---|---|---|
| 21–28 | | | | 240 | 20 | 1 | 91.7 | 99.6 |
| 38–35 | | | | 252 | 33 | 0 | 86.9 | 100 |
| 7–35 | | | | 1132 | 204 | 2 | 82.0 | 99.8 |
| 0–7 | 8 | 25 | 25 | 298 | 22 | 0 | 92.7 | 100 |
| 7–14 | | | | 301 | 47 | 0 | 84.4 | 100 |
| 14–21 | | | | 385 | 15 | 0 | 96.1 | 100 |
| 21–28 | | | | 294 | 6 | 0 | 98.0 | 100 |
| 28–35 | | | | 386 | 7 | 0 | 98.1 | 100 |
| 0–28 | | | | 1658 | 97 | 0 | 94.1 | 100 |

TABLE 4

Effect of increasing the exposure period, to a single dose, on immature stages of *R. dominica*

| Time after dosing before emergence (days) | Dose (mg L⁻¹) | Exposure period Short (h) | Long (h) | No. emerged Control (short) | Short dose | Control (long) | Long dose | % reduction Short dose | Long dose |
|---|---|---|---|---|---|---|---|---|---|
| 0–7 | 25 | 6 | 24 | 24 | 3 | 14 | 0 | 87.5 | 100 |
| 7–14 | | | | 164 | 28 | 284 | 0 | 82.9 | 100 |
| 14–21 | | | | 181 | 11 | 234 | 0 | 93.9 | 100 |
| 21–28 | | | | 169 | 5 | 265 | 0 | 97.0 | 100 |
| 28–35 | | | | 180 | 7 | 355 | 1 | 96.1 | 99.7 |
| 0–35 | | | | 718 | 54 | 1152 | 1 | 92.4 | 99.91 |
| 0–7 | 8 | 24 | 48 | 131 | 29 | 298 | 22 | 77.9 | 92.7 |
| 7–14 | | | | 265 | 84 | 301 | 47 | 68.3 | 84.4 |
| 14–21 | | | | 244 | 38 | 385 | 15 | 84.4 | 96.1 |
| 21–28 | | | | 240 | 20 | 294 | 6 | 91.7 | 98.0 |
| 28–35 | | | | 252 | 33 | 380 | 7 | 86.9 | 98.1 |
| 0–35 | | | | 1132 | 204 | 1658 | 97 | 82.0 | 94.1 |
| 0–7 | 25 | 24 | 48 | 131 | 0 | 298 | 0 | 100 | 100 |
| 7–14 | | | | 265 | 1 | 301 | 0 | 99.6 | 100 |
| 14–21 | | | | 244 | 0 | 385 | 0 | 100 | 100 |
| 21–28 | | | | 240 | 1 | 294 | 0 | 99.6 | 100 |
| 28–35 | | | | 252 | 0 | 380 | 0 | 100 | 100 |
| 0–35 | | | | 1132 | 2 | 1658 | 0 | 99.8 | 100 |

TABLE 5

Control of immature stages of *S. oryzae* at 25° C. or 30° C. after 24 H exposure

| Interval after dosing (days) | Dose Low mg L⁻¹ | High | Temp (° C.) | No. emerged in Control | Low dose | High dose | % reduction Low dose | High dose |
|---|---|---|---|---|---|---|---|---|
| 0–7 | 24 | 48 | 25 | 24 | 6 | 0 | 75.0 | 100 |
| 7–14 | | | | 136 | 34 | 3 | 76.1 | 97.8 |
| 14–21 | | | | 106 | 5 | 0 | 95.3 | 100 |
| 21–28 | | | | 102 | 38 | 0 | 62.7 | 100 |
| 28–35 | | | | 55 | 59 | 0 | −7.3 | 100 |
| 7–35 | | | | 423 | 142 | 3 | 66.4 | 99.3 |
| 0–7 | 15 | 45 | 25 | 79 | 79 | 49 | 0 | 38.0 |
| 7–14 | | | | 65 | 73 | 26 | −12.3 | 60.0 |
| 14–21 | | | | 236 | 183 | 8 | 22.4 | 96.7 |
| 21–28 | | | | 1424 | 778 | 202 | 45.3 | 85.8 |
| 0–28 | | | | 1804 | 1113 | 285 | 38.3 | 84.2 |
| 0–7 | 24 | 64.5 | 25 | 0 | 0 | 0 | — | — |
| 7–14 | | | | 69 | 0 | 0 | 100 | 100 |
| 14–21 | | | | 284 | 8 | 0 | 97.2 | 100 |
| 21–28 | | | | 253 | 11 | 0 | 95.7 | 100 |

TABLE 5-continued

Control of immature stages of *S. oryzae*
at 25° C. or 30° C. after 24 H exposure

| Interval after dosing (days) | Dose Low mg L$^{-1}$ | High | Temp (° C.) | No. emerged in Control | Low dose | High dose | % reduction Low dose | High dose |
|---|---|---|---|---|---|---|---|---|
| 28–35 | | | | 184 | 6 | 0 | 96.7 | 100 |
| 0–35 | | | | 790 | 25 | 0 | 96.8 | 100 |
| 0–7 | 25 | 66 | 30 | 2 | 1 | 0 | 50 | 100 |
| 7–14 | | | | 156 | 76 | 38 | 49.3 | 74.6 |
| 14–21 | | | | 139 | 38 | 30 | 72.7 | 78.4 |
| 21–28 | | | | 147 | 12 | 13 | 91.8 | 91.1 |
| 28–35 | | | | 107 | 40 | 12 | 62.6 | 88.8 |
| 0–35 | | | | 545 | 169 | 93 | 69.4 | 82.9 |
| 0–74 | 25 | 66 | 25 | 131 | 25 | 0 | 80.9 | 100 |
| 7–1 | | | | 265 | 67 | 7 | 74.7 | 97.4 |
| 14–21 | | | | 244 | 4 | 0 | 98.4 | 100 |
| 21–28 | | | | 240 | 4 | 0 | 98.2 | 100 |
| 28–39 | | | | 252 | 16 | 0 | 93.7 | 100 |
| 0–35 | | | | 1132 | 116 | 7 | 89.8 | 99.4 |

TABLE 6

Effect of increasing the exposure period,
to a single dosage, on the immature stages of *S. oryzae*

| Interval after dosing (days) | Dose (mg L$^{-1}$) | Exposure period Short (h) | Long (h) | No. emerged Control (short) | Short dose | Control (long) | Long dose | % reduction Short dose | Long dose |
|---|---|---|---|---|---|---|---|---|---|
| 0–7 | 66 | 6 | 24 | 22 | 2 | 2 | 0 | 90.9 | 100 |
| 7–14 | | | | 143 | 48 | 150 | 38 | 66.4 | 74.6 |
| 14–21 | | | | 152 | 14 | 139 | 30 | 90.8 | 78.4 |
| 21–28 | | | | 151 | 17 | 147 | 13 | 88.7 | 91.1 |
| 28–35 | | | | 82 | 65 | 107 | 12 | 20.7 | 88.8 |
| 0–35 | | | | 550 | 146 | 545 | 93 | 73.4 | 82.9 |
| 0–7 | 66 | 24 | 48 | 93 | 0 | 40 | 0 | 100 | 100 |
| 7–14 | | | | 135 | 7 | 70 | 10 | 94.8 | 85.7 |
| 14–21 | | | | 82 | 0 | 60 | 0 | 100 | 100 |
| 21–28 | | | | 70 | 0 | 53 | 0 | 100 | 100 |
| 28–35 | | | | 74 | 0 | 167 | 0 | 100 | 100 |
| 0–35 | | | | 454 | 7 | 390 | 10 | 99.5 | 97.4 |
| 0–7 | 25 | 24 | 48 | 93 | 25 | 40 | 49 | 73.1 | −22.5 |
| 7–14 | | | | 135 | 67 | 70 | 25 | 50.3 | 64.2 |
| 14–21 | | | | 82 | 4 | 60 | 2 | 95.1 | 96.7 |
| 21–28 | | | | 70 | 4 | 53 | 7 | 94.3 | 86.7 |
| 28–35 | | | | 74 | 16 | 167 | 45 | 78.4 | 73.1 |
| 0–35 | | | | 454 | 116 | 390 | 128 | 74.3 | 67.2 |

TABLE 7

Effect of increasing the exposure period,
to a single dosage, on the immature stages of *S. oryzae*

| Interval after dosing (days) | Dose (mg L$^{-1}$) | No. emerged after exposure period (h) 6 | 24 | 48 | 72 | Control No. |
|---|---|---|---|---|---|---|
| 0–7 | 60 | 0 | 0 | 0 | 0 | 1 |
| 7–14 | | 1 | 0 | 0 | 0 | 85 |
| 14–21 | | 15 | 0 | 0 | 0 | 178 |
| 21–28 | | 27 | 0 | 0 | 0 | 119 |
| 28–35 | | 40 | 1 | 0 | 0 | 58 |
| 0–7 | 91 | 0 | — | 0 | 0 | 2 |
| 7–14 | | 13 | — | 1 | 0 | 84 |
| 14–21 | | 10 | — | 0 | 0 | 139 |
| 21–28 | | 13 | — | 0 | 0 | 97 |
| 28–35 | | 38 | — | 0 | 0 | 60 |

TABLE 8

Comparison between carbon disulphide (CS$_2$),
ethyl formate (EtF) and carbonyl sulphide (COS)
in single dosing of wheat for 24h at 25° C.

| Interval after dosing (days) | Species | Dose mg L$^{-1}$ | No. emerged in Control | CS2 | EtF | % reduction CS2 | EtF | COS[a] |
|---|---|---|---|---|---|---|---|---|
| 0–7 | S. oryzae | 24 | 59 | 11 | 54 | 81.4 | 8.5 | |
| 7–14 | | | 266 | 102 | 226 | 61.7 | 15.0 | |
| 14–21 | | | 205 | 29 | 187 | 85.9 | 8.8 | |
| 21–28 | | | 131 | 19 | 155 | 85.5 | −18.3 | |
| 28–35 | | | 66 | 49 | 42 | 25.8 | 36.3 | |
| 0–35 | | | 727 | 210 | 664 | 71.1 | 8.7 | 80.6[a] |
| 0–7 | | 42 | 118 | 11 | 80 | 90.6 | 32.2 | |
| 7–14 | | | 194 | 61 | 147 | 68.6 | 24.2 | |
| 14–21 | | | 125 | 24 | 96 | 80.8 | 24.8 | |
| 21–28 | | | 118 | 2 | 35 | 98.3 | 70.3 | |
| 28–35 | | | 92 | 6 | 33 | 93.5 | 64.1 | |
| 0–35 | | | 647 | 104 | 391 | 83.9 | 65.4 | |
| 0–7 | R. dominica | 8 | 126 | 107 | 128 | 15.0 | −1.6 | |
| 7–14 | | | 630 | 423 | 516 | 32.8 | 18.1 | |
| 14–21 | | | 421 | 357 | 488 | 15.2 | 15.9 | |
| 21–28 | | | 527 | 326 | 302 | 38.1 | 42.7 | |
| 28–35 | | | 267 | 274 | 284 | −2.6 | −6.3 | |
| 0–35 | | | 1971 | 1487 | 1718 | 24.5 | 12.8 | 93.2[b] |
| 0–7 | | 15 | 186 | 144 | 157 | 22.6 | 15.6 | |
| 7–14 | | | 270 | 175 | 285 | 35.1 | −5.5 | |
| 14–21 | | | 265 | 231 | 245 | 12.8 | 7.5 | |
| 21–28 | | | 290 | 150 | 116 | 48.2 | 63.4 | |
| 28–39 | | | 244 | 116 | 95 | 52.4 | 61.1 | |
| 0–35 | | | 1255 | 816 | 898 | 35.0 | 28.4 | 98.3[c] |

[a]Mean of 4 replicates at this dose
[b]Mean of 5 replicates at this dose
[c]One replicate at this dose

TABLE 9

Toxicity of carbonyl sulphide to adult psocids
(Liposcelis bostrychophilus)

| Temperature (° C.) | Exposure period (h) | Dose (mg h L$^{-1}$) | Mortality Treated (a) | Control | Corrected mortality (%) |
|---|---|---|---|---|---|
| 30 | 6 | 5.4 | 28/200 | 0/200 | 14.0 |
| | | 10.8 | 100/200 | | 50.0 |
| | | 22.5 | 200/200 | | 100 |
| | | 45 | 200/200 | | 100 |
| | 24 | 180 | 200/200 | 5/200 | 100 |

(a) Numbers estimated

TABLE 10

Toxicity of carbonyl sulphide to adults
of (L. destructor)

| Temperature (° C.) | Exposure period (h) | Dose (mg h L$^{-1}$) | Mortality Treated (a) | Control | Corrected mortality (%) |
|---|---|---|---|---|---|
| 25 | 6 | 120 | 43/43 | 10/135 | 100 |
| | 24 | 360 | 35/35 | 3/53 | 100 |
| | | 240 | 241/241 | 7/167 | 100 |
| | | 120 | 339/340 | | 99.7 |

TABLE 11

Toxicity of carbonyl sulphide to pupae of B. tyroni

| Temperature (° C.) | Exposure period (h) | Dose (mg h L$^{-1}$) | Mortality Treated | Control | Corrected mortality (%) |
|---|---|---|---|---|---|
| 30 | 6 | 600 | 40/40 | 0/40 | 100 |
| | | 360 | 60/60 | | 100 |
| | | 300 | 55/60 | | 91.7 |
| | | 240 | 33/60 | | 55.0 |
| | | 180 | 11/80 | | 13.8 |
| | 24 | 600 | 40/40 | 0/40 | 100 |
| | | 540 | 59/60 | | 98.3 |
| | | 480 | 59/60 | | 98.3 |
| | | 420 | 71/80 | | 88.8 |
| | | 366 | 32/60 | | 53.3 |
| | | 300 | 5/55 | | 9.1 |

TABLE 12

Toxicity of carbonyl sulphide to late instar larvae
of B. tyroni

| Temperature (° C.) | Exposure period (h) | Dose (mg h L$^{-1}$) | Mortality Treated | Control | Corrected mortality (%) |
|---|---|---|---|---|---|
| 30 | 24 | 600 | 60/60 | 2/17 | 100 |
| | | 360 | 60/60 | | 100 |
| | | 120 | 13/31 | | 37.1 |
| | 6 | 360 | 60/60 | | 100 |
| | | 120 | 15/78 | | 12.6 |

TABLE 12-continued

Toxicity of carbonyl sulphide to late instar larvae of *B. tyroni*

| Temperature (° C.) | Exposure period (h) | Dose (mg h L$^{-1}$) | Mortality Treated | Mortality Control | Corrected mortality (%) |
|---|---|---|---|---|---|
| | 24 | 240 | 4/36 | — | |
| | | 180 | 9/38 | — | |
| | 6 | 240 | 37/37 | 18/47 | 100 |
| | | 210 | 34/34 | | 100 |
| | | 180 | 33/33 | | 100 |
| | | 150 | 32/33 | | |
| | | 120 | 41/50 | | |

TABLE 13

Toxicity of carbonyl sulphide to eggs of *B. tyroni*

| Age (d) | Temperature (° C.) | Exposure period (h) | Dose (mg h L$^{-1}$) | Mortality Treated | Mortality Control | Corrected mortality (%) |
|---|---|---|---|---|---|---|
| 0.08–0.3 | 30 | 24 | 600 | 116/116 | 23/111 | 100 |
| | | | 540 | 130/133 | | 97.1 |
| | | | 480 | 90/92 | | 97.3 |
| | | | 420 | 80/104 | | 70.9 |
| | | | 360 | 92/112 | | 77.5 |
| | | | 180 | 60/515 | 17/239 | 4.9 |
| | | | 240 | 101/401 | | 19.5 |
| | | | 300 | 356/521 | | 65.9 |
| | | 6 | 240 | 265/407 | 17/343 | 63.2 |
| | | | 360 | 373/399 | | 93.1 |
| | | | 480 | 517/521 | | 99.19 |
| | | | 600 | 450/452 | | 99.53 |
| | | 6 | 720 | 483/484 | 17/285 | 99.73 |
| | | | 870 | 118/126 | 81/327 | 93.3 |
| | | | 180 | 198/336 | | 45.4 |
| | | | 150 | 122/349 | | 13.5 |

TABLE 14

Toxicity of carbonyl sulphide to adults of *Coptotermes acinaciformis*

| Temperature (° C.) | Exposure period (h) | Dose (mg h L$^{-1}$) | Mortality Treated (a) | Mortality Control | Corrected mortality (%) |
|---|---|---|---|---|---|
| 25 | 24 | 600 | 165/165 | 0/100 | 100 |
| | | 288 | 110/110 | | 100 |
| | | 192 | 0/165 | | 0 |
| | 6 | 120 | 11/113 | | 9.7 |
| | | 96 | 3/110 | | 2.7 |

TABLE 15

Toxicity of carbonyl sulphide to nymphs of *Coptotermes acinaciformis*

| Temperature (° C.) | Exposure period (h) | Dose (mg h L$^{-1}$) | Mortality Treated (a) | Mortality Control | Corrected mortality (%) |
|---|---|---|---|---|---|
| 25 | 24 | 600 | 30/30 | 0/30 | 100 |
| | | 192 | 0/30 | | 0 |

TABLE 16

Effect of carbonyl sulphide on germination of wheat of 16.0% moisture content

| Concentration %, V/V | % Germination First count (4 days) | % Germination Final count (10 days) |
|---|---|---|
| 0 | 85 | 90 |
| | 90 | 91 |
| | 87 | 87 |
| 0.5 | 93 | 96 |
| | 91 | 93 |
| 1.0 | 93 | 93 |
| | 89 | 92 |
| 5.0 | 89 | 93 |
| | 93 | 93 |

TABLE 17

Raw data for absorption of carbonyl sulphide on wheat of 11.7% moisture content, at 25° C., and at initial concentrations of 48–52 mg L$^{-1}$

| Time after dosing (h) | Concentration for degree of fill (mg L$^{-1}$) 0% | | 25% | | 50% | | 95% | |
|---|---|---|---|---|---|---|---|---|
| Applied | 45.0 | 44.9 | 47.7 | 47.5 | 49.2 | 48.4 | 52.2 | 51.5 |
| 0.25 | 44.3 | 44.2 | 45.7 | 45.6 | 45.9 | 45.7 | 46.4 | 46.0 |
| 0.75 | 44.8 | 44.8 | 45.4 | 45.2 | 43.6 | 43.5 | 44.9 | 44.8 |
| 1.28 | 44.9 | 44.8 | 45.0 | 45.0 | 42.0 | 41.8 | 43.6 | 43.5 |
| 3.35 | 44.5 | 44.5 | 43.5 | 43.3 | 40.7 | 40.2 | 40.3 | 39.8 |
| 21.7 | 44.8 | 44.9 | 43.1 | 43.0 | 37.0 | 36.6 | 30.8 | 30.6 |
| 27.5 | 44.8 | 45.0 | 44.1 | 44.0 | 36.8 | 36.8 | 29.5 | 29.3 |
| 42.5 | 44.7 | 44.0 | 41.2 | 41.3 | 35.4 | 35.2 | 24.5 | 24.5 |
| 50.0 | 44.0 | 44.0 | 40.5 | 40.6 | 33.6 | 33.8 | 22.2 | 22.0 |
| 68.3 | 43.7 | 43.7 | 39.0 | 39.1 | 33.1 | 33.1 | 17.8 | 17.7 |
| 73.5 | 43.7 | 43.0 | 39.7 | 39.7 | 32.5 | 32.5 | 16.7 | 16.6 |
| 93.9 | 43.8 | 43.9 | 37.0 | 37.1 | 31.1 | 30.8 | 13.4 | 13.3 |

TABLE 18

Toxicity of carbonyl sulphide to a mixed culture of *S. oryzae* with various concentrations of carbonyl sulphide for various exposure periods

| Days after dosing | Number of insects emerging from culture for exposure (in hours) × concentration (in mg L$^{-1}$) 6 × 200 | 6 × 120 | 24 × 80 | 24 × 60 |
|---|---|---|---|---|
| 7 | 0 | 3 | 0 | 0 |
| 14 | 3 | 5 | 0 | 0 |
| 21 | 0 | 2 | 0 | 0 |
| 28 | 0 | 3 | 0 | 0 |
| 35 | 2 | 6 | 0 | 0 |

| Days after dosing | Number of insects emerging from culture for exposure (in hours) × concentration (in mg L$^{-1}$) 48 × 60 | 48 × 40 | 48 × 30 | Control |
|---|---|---|---|---|
| 7 | 0 | 0 | 0 | 8 |
| 14 | 0 | 0 | 2 | 93 |
| 21 | 0 | 0 | 0 | 87 |
| 28 | 0 | 0 | 0 | 36 |
| 35 | 0 | 0 | 0 | 36 |

TABLE 18-continued

Toxicity of carbonyl sulphide to a mixed culture of
S. oryzae with various concentrations of carbonyl
sulphide for various exposure periods

| Days after dosing | Number of insects emerging from culture for exposure (in hours) × concentration (in mg L⁻¹) | | | |
|---|---|---|---|---|
| | 72 × 40 | 72 × 30 | 72 × 20 | 168 × 30 |
| 7 | 0 | 0 | 0 | 0 |
| 14 | 0 | 0 | 3 | 0 |
| 21 | 0 | 0 | 1 | 0 |
| 28 | 0 | 0 | 0 | 0 |
| 35 | 0 | 0 | 3 | 0 |

| Days after dosing | Number of insects emerging from culture for exposure (in hours) × concentration (in mg L⁻¹) | | |
|---|---|---|---|
| | 168 × 20 | 168 × 10 | Control |
| 7 | 0 | 1 | 8 |
| 14 | 0 | 0 | 93 |
| 21 | 0 | 1 | 87 |
| 28 | 0 | 36 | 36 |
| 35 | 0 | 27 | 36 |

TABLE 19

Control of nematodes in soil with carbonyl sulphide

| Soil Sample | Quantity (grams) | Calculated concentration of COS(mg L⁻¹) | % kill of nematode |
|---|---|---|---|
| A1 | 30 | 28 | 42.6 |
| A2 | 30 | 280 | 89.5 |
| A control | | | 0 |
| B1 | 39 | 28 | 54.4 |
| B2 | 38 | 560 | 37.8 |
| B3 | 1000 | 28 | 94.0 |
| B control | | | 0 |
| C1 | 40 | 140 | 7 |
| C2 | 40 | 28 | 28 |
| C control | | | 0 |

What is claimed is:

1. A method of controlling a pest in a stored product, timber, soil or a space, said method comprising applying a dose of carbonyl sulphide to the stored product, timber, soil or space, wherein the dose is sufficient to control said pest, and wherein said pest is selected from the group consisting of insects, nematodes, and mites.

2. A method as claimed in claim 1, wherein the stored product is fruit, and the carbonyl sulphide is gaseous carbonyl sulphide that is applied for at least 6 hours at a concentration that is sufficient to control all immature stages of fruit fly.

3. A method as claimed in claim 1, wherein the carbonyl sulphide is applied to timber, a wood product or a building containing wood at a concentration sufficient to control termites or other timber pests.

4. A method as claimed in claim 1, wherein the carbonyl sulphide is applied to soil at a concentration sufficient to control nematodes.

5. A method as claimed in claim 1, wherein control comprises achieving a mortality of 95 percent of the pest over a 6-hour period and in which:
(a) when the pest is adult *Rhyzopertha dominica*, the dose of carbonyl sulphide comprises at least 6.3 mg L⁻¹;
(b) when the pest is adult *Tribolium castaneum*, the dose of carbonyl sulphide comprises at least 13.7 mg L⁻¹;
(c) when the pest is adult *Sitophilus oryzae*, the dose of carbonyl sulphide comprises at least 16.5 mg L⁻¹;
(d) when the pest is adult *Tribolium confusum*, the dose of carbonyl sulphide comprises at least 18.5 mg L⁻¹; and
(e) when the pest is adult *Oryzaephilus surinamensis*, the dose of carbonyl sulphide comprises at least 33 mg L⁻¹.

6. A method as claimed in claim 1, wherein control comprises achieving a mortality of 95 percent of the pest, and in which:
(a) when the pest is adult *Rhyzopertha dominica*, the dose of carbonyl sulphide comprises at least 38 mg h. L⁻¹;
(b) when the pest is adult *Tribolium castaneum*, the dose of carbonyl sulphide comprises at least 82 mg h. L⁻¹;
(c) when the pest is adult *Sitophilus oryzae*, the dose of carbonyl sulphide comprises at least 99 mg h. L⁻¹;
(d) when the pest is adult *Oryzaephilus surinamensis*, the dose of carbonyl sulphide comprises at least 198 mg h. L⁻¹;
(e) when the pest is adult *Tribolium confusum*, the dose of carbonyl sulphide comprises at least 111 mg h. L⁻¹;
(f) when the pest is adult *Lepidoglyphus destructor*, the dose of carbonyl sulphide comprises at least 240 mg h. L⁻¹;
(g) when the pest is pupae of *T. castaneum*, the dose of carbonyl sulphide comprises at least 290 mg h. L⁻¹;
(h) when the pest is pupae of *B. tyroni*, the dose of carbonyl sulphide comprises at least 440 mg h. L⁻¹;
(i) when the pest is larvae of *T. castaneum*, the dose of carbonyl sulphide comprises at least 270 mg h. L⁻¹;
(j) when the pest is larvae of *E. cautella*, the dose of carbonyl sulphide comprises at least 410 mg h. L⁻¹;
(k) when the pest is larvae of *O. surinamensis*, the dose of carbonyl sulphide comprises at least 210 mg h. L⁻¹;
(l) when the pest is eggs of *R. dominica*, the dose of carbonyl sulphide comprises at least 102 mg h. L⁻¹;
(m) when the pest is eggs of *T. castaneum*, the dose of carbonyl sulphide comprises at least 430 mg h. L⁻¹;
(n) when the pest is eggs of *O. surinamensis*, the dose of carbonyl sulphide comprises at least 495 mg h. L⁻¹; and
(o) when the pest is eggs of *B. tyroni*, the dose of carbonyl sulphide comprises at least 460 mg h. L⁻¹.

7. A method as claimed in claim 1, wherein the dose of carbonyl sulphide is applied to timber, a wood product, or a building containing wood, wherein control comprises achieving a mortality of 95 percent of the pest over a 6-hour period, and wherein:
(a) when the pest is adult *Rhyzopertha dominica*, the dose of carbonyl sulphide comprises at least 6.3 mg L⁻¹;
(b) when the pest is adult *Tribolium castaneum*, the dose of carbonyl sulphide comprises at least 13.7 mg L⁻¹;
(c) when the pest is adult *Sitophilus oryzae*, the dose of carbonyl sulphide comprises at least 16.5 mg L⁻¹;
(d) when the pest is adult *Tribolium confusum*, the dose of carbonyl sulphide comprises at least 18.5 mg L⁻¹; and
(e) when the pest is adult *Oryzaephilus surinamensis*, the dose of carbonyl sulphide comprises at least 33 mg L⁻¹.

8. A method as claimed in claim 1, wherein control comprises achieving a mortality of 95 percent of a selected food pest, and in which:
(a) when the selected food pest is adult *Rhyzopertha dominica* at 25° C., the dose of carbonyl sulphide comprises at least 38 mg h. L⁻¹;
(b) when the selected food pest is adult *Tribolium castaneum* at 25° C., the dose of carbonyl sulphide comprises at least 82 mg h. L⁻¹;

(c) when the selected food pest is adult *Sitophilus oryzae* at 25° C., the dose of carbonyl sulphide comprises at least 99 mg h. L$^{-1}$;

(d) when the selected food pest is adult *Oryzaephilus surinamensis* at 25° C., the dose of carbonyl sulphide comprises at least 198 mg h. L$^{-1}$;

(e) when the selected food pest is adult *Tribolium confusum* at 25° C., the dose of carbonyl sulphide comprises at least 111 mg h. L$^{-1}$;

(f) when the selected food pest is adult *Lepidoglyphus destructor* at 25° C., the dose of carbonyl sulphide comprises at least 240 mg h. L$^{-1}$;

(g) when the selected pest is pupae of *T. castaneum* at 30° C., the dose of carbonyl sulphide comprises at least 290 mg h. L$^{-1}$;

(h) when the selected pest is pupae of *B. tyroni* at 27° C., the dose of carbonyl sulphide comprises at least 440 mg h. L$^{-1}$;

(i) when the selected pest is larvae of *T. castaneum* at 25° C., the dose of carbonyl sulphide comprises at least 270 mg h. L$^{-1}$;

(j) when the selected pest is larvae of *E. cautella*, the dose of carbonyl sulphide comprises at least 410 mg h. L$^{-1}$;

(k) when the selected pest is larvae of *O. surinamensis*, the dose of carbonyl sulphide comprises at least 210 mg h. L$^{-1}$;

(l) when the selected pest is eggs of *R. dominica*, the dose of carbonyl sulphide comprises at least 102 mg h. L$^{-1}$;

(m) when the selected pest is eggs of *T.castaneum*, the dose of carbonyl sulphide comprises at least 430 mg h. L$^{-1}$;

(n) when the selected pest is eggs of *O. surinamensis*, the dose of carbonyl sulphide comprises at least 495 mg h. L$^{-1}$; and (o) when the selected pest is eggs of *B. tyroni*, the dose of carbonyl sulphide comprises at least 460 mg h. L$^{-1}$.

9. A method as claimed in claim 1, wherein control comprises achieving a mortality of 95 percent of the pest over a 6-hour period and in which the dose of carbonyl sulphide comprises at least 6.3 mg L$^{-1}$.

10. A method as claimed in claim 1, in which control comprises achieving a mortality of 95 percent of the pest, and in which the dose of carbonyl sulphide comprises at least 38 mg h. L$^{-1}$.

11. A method as claimed in claim 1, wherein control comprises achieving a mortality of 95 percent of the pest over a 6-hour period and in which the dose of carbonyl sulphide comprises at least 16.5 mg L$^{-1}$.

12. A method as claimed in claim 1, in which control comprises achieving a mortality of 95 percent of the pest, and in which the dose of carbonyl sulphide comprises at least 99 mg h. L$^{-1}$.

13. A method as claimed in claim 1, wherein the stored product comprises grain, fruit, or another food.

14. A method as claimed in claim 13, in which the control comprises achieving a mortality of 95 percent of the pest at 25° C., and in which
(a) when the pest is adult *Rhyzopertha dominica*, the dose of carbonyl sulphide comprises at least 38 mg h. L$^{-1}$;
(b) when the pest is adult *Tribolium castaneum*, the dose of carbonyl sulphide comprises at least 82 mg h. L$^{-1}$;
(c) when the pest is adult *Sitophilus oryzae*, the dose of carbonyl sulphide comprises at least 99 mg h. L$^{-1}$;
(d) when the pest is adult *Tribolium confusum*, the dose of carbonyl sulphide comprises at least 111 mg h. L$^{-1}$; and
(e) when the pest is adult *Oryzaephilus surinamensis*, the dose of carbonyl sulphide comprises at least 198 mg h. L$^{-1}$.

15. A method as claimed in claim 13, in which control comprises achieving a mortality of 95 percent of the pest, and in which:
(a) when the pest is adult *Rhyzopertha dominica* at 25° C., the dose of carbonyl sulphide comprises at least 38 mg h. L$^{-1}$;
(b) when the pest is adult *Tribolium castaneum* at 25° C., the dose of carbonyl sulphide comprises at least 82 mg h. L$^{-1}$;
(c) when the pest is adult *Sitophilus oryzae* at 25° C., the dose of carbonyl sulphide comprises at least 99 mg h. L$^{-1}$;
(d) when the pest is adult *Oryzaephilus surinamensis* at 25° C., the dose of carbonyl sulphide comprises at least 198 mg h. L$^{-1}$;
(e) when the pest is adult *Tribolium confusum* at 25° C., the dose of carbonyl sulphide comprises at least 111 mg h. L$^{-1}$;
(f) when the pest is adult *Lepidoglyphus destructor* at 25° C., the dose of carbonyl sulphide comprises at least 240 mg h. L$^{-1}$;
(g) when the pest is pupae of *T. castaneum* at 30° C., the dose of carbonyl sulphide comprises at least 290 mg h. L$^{-1}$;
(h) when the pest is pupae of *B. tyroni* at 27° C., the dose of carbonyl sulphide comprises at least 440 mg h. L$^{-1}$;
(i) when the pest is larvae of *T. castaneum* at 25° C., the dose of carbonyl sulphide comprises at least 270 mg h. L$^{-1}$;
(j) when the pest is larvae of *E. cautella*, the dose of carbonyl sulphide comprises at least 410 mg h. L$^{-1}$;
(k) when the pest is larvae of *O. surinamensis*, the dose of carbonyl sulphide comprises at least 210 mg h. L$^{-1}$;
(l) when the pest is eggs of *R. dominica*, the dose of carbonyl sulphide comprises at least 102 mg h. L$^{-1}$;
(m) when the pest is eggs of *T. castaneum*, the dose of carbonyl sulphide comprises at least 430 mg h. L$^{-1}$;
(n) when the pest is eggs of *O. surinamensis*, the dose of carbonyl sulphide comprises at least 495 mg h. L$^{-1}$; and
(o) when the pest is eggs of *B. tyroni*, the dose of carbonyl sulphide comprises at least 460 mg h. L$^{-1}$.

16. A method as claimed in claim 13, wherein control comprises achieving a mortality of 95 percent of the pest over a 6-hour period and in which:
(a) when the selected food pest is adult *Rhyzopertha dominica*, the dose of carbonyl sulphide comprises at least 6.3 mg L$^{-1}$;
(b) when the selected food pest is adult *Tribolium castaneum*, the dose of carbonyl sulphide comprises at least 13.7 mg L$^{-1}$;
(c) when the selected food pest is adult *Sitophilus oryzae*, the dose of carbonyl sulphide comprises at least 16.5 mg L$^{-1}$;
(d) when the selected food pest is adult *Tribolium confusum*, the dose of carbonyl sulphide comprises at least 18.5 mg L$^{-1}$; and
(e) when the selected food pest is adult *Oryzaephilus surinamensis*, the dose of carbonyl sulphide comprises at least 33 mg L$^{-1}$.

17. A method as claimed in claim 13, wherein control comprises achieving a mortality of 95 percent of the pest, and in which:

(a) when the pest is adult *Rhyzopertha dominica*, the dose of carbonyl sulphide comprises at least 38 mg h. $L^{-1}$;
(b) when the pest is adult *Tribolium castaneum*, the dose of carbonyl sulphide comprises at least 82 mg h. $L^{-1}$;
(c) when the pest is adult *Sitophilus oryzae*, the dose of carbonyl sulphide comprises at least 99 mg h. $L^{-1}$;
(d) when the selected food pest is adult *Oryzaephilus surinamensis*, the dose of carbonyl sulphide comprises at least 198 mg h. $L^{-1}$;
(e) when the pest is adult *Tribolium confusum*, the dose of carbonyl sulphide comprises at least 111 mg h. $L^{-1}$;
(f) when the pest is adult *Lepidoglyphus destructor*, the dose of carbonyl sulphide comprises at least 240 mg h. $L^{-1}$;
(g) when the pest is pupae of *T. castaneum*, the dose of carbonyl sulphide comprises at least 290 mg h. $L^{-1}$;
(h) when the pest is pupae of *B. tyroni*, the dose of carbonyl sulphide comprises at least 440 mg h. $L^{-1}$;
(i) when the pest is larvae of *T. castaneum*, the dose of carbonyl sulphide comprises at least 270 mg h. $L^{-1}$;
(j) when the pest is larvae of *E. cautella*, the dose of carbonyl sulphide comprises at least 410 mg h. $L^{-1}$;
(k) when the pest is larvae of *O. surinamensis*, the dose of carbonyl sulphide comprises at least 210 mg h. $L^{-1}$;
(l) when the pest is eggs of *R. dominica*, the dose of carbonyl sulphide comprises at least 102 mg h. $L^{-1}$;
(m) when the pest is eggs of *T. castaneum*, the dose of carbonyl sulphide comprises at least 430 mg h. $L^{-1}$;
(n) when the pest is eggs of *O. surinamensis*, the dose of carbonyl sulphide comprises at least 495 mg h. $L^{-1}$; and
(o) when the pest is eggs of *B. tyroni*, the dose of carbonyl sulphide comprises at least 460 mg h. $L^{-1}$.

18. A method as claimed in claim 13, wherein the dose of carbonyl sulphide is applied to timber, a wood product, or a building containing wood, wherein control comprises achieving a mortality of 95 percent of the pest over a 6-hour period, and wherein:
(a) when the pest is adult *Rhyzopertha dominica*, the dose of carbonyl sulphide comprises at least 6.3 mg $L^{-1}$;
(b) when the pest is adult *Tribolium castaneum*, the dose of carbonyl sulphide comprises at least 13.7 mg $L^{-1}$;
(c) when the pest is adult *Sitophilus oryzae*, the dose of carbonyl sulphide comprises at least 16.5 mg $L^{-1}$;
(d) when the pest is adult *Tribolium confusum*, the dose of carbonyl sulphide comprises at least 18.5 mg $L^{-1}$; and
(e) when the pest is adult *Oryzaephilus surinamensis*, the dose of carbonyl sulphide comprises at least 33 mg $L^{-1}$.

19. A method as claimed in claim 13, wherein control comprises achieving a mortality of 95 percent of the pest over a 6-hour period and in which the dose of carbonyl sulphide comprises at least 6.3 mg $L^{-1}$.

20. A method as claimed in claim 13, in which control comprises achieving a mortality of 95 percent of the pest, and in which the dose of carbonyl sulphide comprises at least 38 mg h. $L^{-1}$.

21. A method as claimed in claim 13, wherein control comprises achieving a mortality of 95 percent of the pest over a 6-hour period and in which the dose of carbonyl sulphide comprises at least 16.5 mg $L^{-1}$.

22. A method as claimed in claim 13, in which control comprises achieving a mortality of 95 percent of the pest, and in which the dose of carbonyl sulphide comprises at least 99 mg h. $L^{-1}$.

23. A method as claimed in claim 1, wherein the dose of carbonyl sulphide is applied for a period of from 1 hour to 35 days.

24. A method as claimed in claim 23, wherein control comprises achieving a mortality of 95 percent of the pest over a 6-hour period and in which:
(a) when the selected food pest is adult *Rhyzopertha dominica*, the dose of carbonyl sulphide comprises at least 6.3 mg $L^{-1}$;
(b) when the selected food pest is adult *Tribolium castaneum*, the dose of carbonyl sulphide comprises at least 13.7 mg $L^{-1}$;
(c) when the selected food pest is adult *Sitophilus oryzae*, the dose of carbonyl sulphide comprises at least 16.5 mg $L^{-1}$;
(d) when the selected food pest is adult *Tribolium confusum*, the dose of carbonyl sulphide comprises at least 18.5 mg $L^{-1}$; and
(e) when the selected food pest is adult *Oryzaephilus surinamensis*, the dose of carbonyl sulphide comprises at least 33 mg $L^{-1}$.

25. A method as claimed in claim 23, wherein control comprises achieving a mortality of 95 percent of the pest over a 6-hour period and in which the dose of carbonyl sulphide comprises at least 6.3 mg $L^{-1}$.

26. A method as claimed in claim 23, in which control comprises achieving a mortality of 95 percent of the pest, and in which the dose of carbonyl sulphide comprises at least 38 mg h. $L^{-1}$.

27. A method as claimed in claim 23, wherein control comprises achieving a mortality of 95 percent of the pest over a 6-hour period and in which the dose of carbonyl sulphide comprises at least 16.5 mg $L^{-1}$.

28. A method as claimed in claim 23, in which control comprises achieving a mortality of 95 percent of the pest, and in which the dose of carbonyl sulphide comprises at least 99 mg h. $L^{-1}$.

29. A method of controlling a pest in an area, the method comprising applying a dose of carbonyl sulphide to the area, wherein the dose is sufficient to control the pest, and wherein the pest is selected from the group consisting of insects, nematodes, and mites.

30. A method as claimed in claim 29, wherein the area comprises air; and wherein applying the dose of the carbonyl sulphide comprises adding the carbonyl sulphide to the air.

31. A method as claimed in claim 30, wherein the area further comprises a stored product, timber, or soil.

32. A method as claimed in claim 30, wherein, after the dose of the carbonyl sulphide is applied, the carbonyl sulphide in the air has a concentration of 5–560 mg $L^{-1}$.

33. A method as claimed in claim 30, wherein, after the dose of the carbonyl sulphide is applied, the carbonyl sulphide in the air has a concentration of 16.5–280 mg $L^{-1}$.

34. A method as claimed in claim 30, wherein, after the dose of the carbonyl sulphide is applied, the carbonyl sulphide in the air has a concentration of 15–200 mg $L^{-1}$.

35. A method as claimed in claim 30, wherein, after the dose of the carbonyl sulphide is applied, the carbonyl sulphide in the air has a concentration of 15–120 mg $L^{-1}$.

36. A method as claimed in claim 30, wherein, after the dose of the carbonyl sulphide is applied, the carbonyl sulphide in the air has a concentration of 15–91 mg $L^{-1}$.

37. A method as claimed in claim 30, wherein, after the dose of the carbonyl sulphide is applied, the carbonyl sulphide in the air has a concentration ranging up to 560 mg $L^{-1}$; and wherein:
(a) when the pest is adult *Rhyzopertha dominica*, the concentration of the carbonyl sulphide in the air is at least 6.3 mg $L^{-1}$;

(b) when the pest is adult *Tribolium castaneum*, the concentration of the carbonyl sulphide in the air is at least 13.7 mg $L^{-1}$;

(c) when the pest is adult *Sitophilus oryzae*, the concentration of the carbonyl sulphide in the air is at least 16.5 mg $L^{-1}$;

(d) when the selected food pest is adult *Tribolium confusum*, the concentration of the carbonyl sulphide in the air is at least 18.5 mg $L^{-1}$; and (e) when the selected food pest is adult *Oryzaephilus surinamensis*, the concentration of the carbonyl sulphide in the air is at least 33 mg $L^{-1}$.

38. A method as claimed in claim 37, wherein control comprises achieving a mortality of at least 95 percent of the pest.

39. A method as claimed in claim 37, wherein control comprises achieving a mortality of at least 95 percent of the pest over a 6-hour period.

40. A method as claimed in claim 30, wherein the dose of the carbonyl sulphide is 22.5 to 6552 mg h. $L^{-1}$.

41. A method as claimed in claim 30, wherein the dose of the carbonyl sulphide is 22.5 to 2880 mg h. $L^{-1}$.

42. A method as claimed in claim 30, wherein the dose of the carbonyl sulphide is 22.5 to 1440 mg h. $L^{-1}$.

43. A method as claimed in claim 30, wherein the dose of the carbonyl sulphide is 22.5 to 600 mg h. $L^{-1}$.

44. A method as claimed in claim 30, wherein the dose of the carbonyl sulphide ranges up to 6552 mg h. $L^{-1}$; and wherein:

(a) when the pest is adult *Rhyzopertha dominica*, the dose of the carbonyl sulphide is at least 38 mg h. $L^{-1}$;

(b) when the pest is adult *Tribolium castaneum*, the dose of the carbonyl sulphide is at least 82 mg h. $L^{-1}$;

(c) when the pest is adult *Sitophilus oryzae*, the dose of the carbonyl sulphide is at least 99 mg h. $L^{-1}$;

(d) when the pest is adult *Oryzaephilus surinamensis*, the dose of the carbonyl sulphide is at least 198 mg h. $L^{-1}$;

(e) when the pest is adult *Tribolium confusum*, the dose of the carbonyl sulphide is at least 111 mg h. $L^{-1}$;

(f) when the pest is adult *Lepidoglyphus destructor* at 25° C., the dose of the carbonyl sulphide is at least 240 mg h. $L^{-1}$;

(g) when the pest is pupae of *T. castaneum*, the dose of the carbonyl sulphide is at least 290 mg h. $L^{-1}$;

(h) when the pest is pupae of *B. tyroni*, the dose of the carbonyl sulphide is at least 440 mg h. $L^{-1}$;

(i) when the pest is larvae of *T. castaneum*, the dose of the carbonyl sulphide is at least 270 mg h. $L^{-1}$;

(j) when the pest is larvae of *E. cautella*, the dose of the carbonyl sulphide is at least 410 mg h. $L^{-1}$;

(k) when the pest is larvae of *O. surinamensis*, the dose of the carbonyl sulphide is at least 210 mg h. $L^{-1}$;

(l) when the pest is eggs of *R. dominica*, the dose of the carbonyl sulphide is at least 102 mg h. $L^{-1}$;

(m) when the pest is eggs of *T. castaneum*, the dose of the carbonyl sulphide is at least 430 mg h. $L^{-1}$;

(n) when the pest is eggs of *O. surinamensis*, the dose of the carbonyl sulphide is at least 495 mg h. $L^{-1}$; and (o) when the pest is eggs of *B. tyroni*, the dose of the carbonyl sulphide is at least 460 mg h. $L^{-1}$.

45. A method as claimed in claim 44, wherein control comprises achieving a mortality of at least 95 percent of the pest.

46. A method as claimed in claim 44, wherein control comprises achieving a mortality of at least 95 percent of the pest over a 6-hour period.

47. A method as claimed in claim 29, wherein the area comprises a gas; and wherein applying the dose of the carbonyl sulphide comprises adding the carbonyl sulphide to the gas.

48. A method as claimed in claim 47, wherein, after the dose of the carbonyl sulphide is applied, the carbonyl sulphide in the gas has a concentration of 5–560 mg $L^{-1}$.

49. A method as claimed in claim 47, wherein the dose of the carbonyl sulphide is 22.5 to 5040 mg h. $L^{-1}$.

50. A method for protecting a foodstuff that is consumed by a mammal, wherein the foodstuff is stored in an area, the method comprising:

applying a dose of carbonyl sulphide to the foodstuff, wherein the dose is sufficient to control a pest selected from the group consisting of insects, nematodes, and mites.

51. A method as claimed in claim 50, wherein the area comprises air; and wherein applying the dose of the carbonyl sulphide comprises adding the carbonyl sulphide to the air.

52. A method as claimed in claim 51, wherein, after the dose of the carbonyl sulphide is applied, the carbonyl sulphide in the air has a concentration ranging up to 560 mg $L^{-1}$; and wherein:

(a) when the pest is adult *Rhyzopertha dominica*, the concentration of the carbonyl sulphide in the air is at least 6.3 mg $L^{-1}$;

(b) when the pest is adult *Tribolium castaneum*, the concentration of the carbonyl sulphide in the air is at least 13.7 mg $L^{-1}$;

(c) when the pest is adult *Sitophilus oryzae*, the concentration of the carbonyl sulphide in the air is at least 16.5 mg $L^{-1}$;

(d) when the selected food pest is adult *Tribolium confusum*, the concentration of the carbonyl sulphide in the air is at least 18.5 mg $L^{-1}$; and (e) when the selected food pest is adult *Oryzaephilus surinamensis*, the concentration of the carbonyl sulphide in the air is at least 33 mg $L^{-1}$.

53. A method as claimed in claim 51, wherein the dose of the carbonyl sulphide ranges up to 6552 mg h. $L^{-1}$; and wherein:

(a) when the pest is adult *Rhyzopertha dominica*, the dose of the carbonyl sulphide is at least 38 mg h. $L^{-1}$;

(b) when the pest is adult *Tribolium castaneum*, the dose of the carbonyl sulphide is at least 82 mg h. $L^{-1}$;

(c) when the pest is adult *Sitophilus oryzae*, the dose of the carbonyl sulphide is at least 99 mg h. $L^{-1}$;

(d) when the pest is adult *Oryzaephilus surinamensis*, the dose of the carbonyl sulphide is at least 198 mg h. $L^{-1}$;

(e) when the pest is adult *Tribolium confusum*, the dose of the carbonyl sulphide is at least 111 mg h. $L^{-1}$;

(f) when the pest is adult *Lepidoglyphus destructor* at 25° C., the dose of the carbonyl sulphide is at least 240 mg h. $L^{-1}$;

(g) when the pest is pupae of *T. castaneum*, the dose of the carbonyl sulphide is at least 290 mg h. $L^{-1}$;

(h) when the pest is pupae of *B. tyroni*, the dose of the carbonyl sulphide is at least 440 mg h. $L^{-1}$;

(i) when the pest is larvae of *T. castaneum*, the dose of the carbonyl sulphide is at least 270 mg h. $L^{-1}$;

(j) when the pest is larvae of *E. cautella*, the dose of the carbonyl sulphide is at least 410 mg h. $L^{-1}$;

(k) when the pest is larvae of *O. surinamensis*, the dose of the carbonyl sulphide is at least 210 mg h. $L^{-1}$;

(l) when the pest is eggs of *R. dominica*, the dose of the carbonyl sulphide is at least 102 mg h. $L^{-1}$;

(m) when the pest is eggs of *T. castaneum*, the dose of the carbonyl sulphide is at least 430 mg h. $L^{-1}$;

(n) when the pest is eggs of *O. surinamensis*, the dose of the carbonyl sulphide is at least 495 mg h. $L^{-1}$; and (o) when the pest is eggs of *B. tyroni*, the dose of the carbonyl sulphide is at least 460 mg h. $L^{-1}$.

54. A method as claimed in claim 52, wherein control comprises achieving a mortality of at least 95 percent of the pest.

55. A method as claimed in claim 53, wherein control comprises achieving a mortality of at least 95 percent of the pest.

* * * * *